US011471555B2

(12) United States Patent
Schoolfield et al.

(10) Patent No.: US 11,471,555 B2
(45) Date of Patent: Oct. 18, 2022

(54) METHODS OF REDUCING TRIMETHYLAMINE

(71) Applicant: International Paper Company, Memphis, TN (US)

(72) Inventors: Mary Virginia Schoolfield, Seattle, WA (US); Hugh West, Seattle, WA (US)

(73) Assignee: INTERNATIONAL PAPER COMPANY, Memphis, TN (US)

( * ) Notice: Subject to any disclaimer, the term of this patent is extended or adjusted under 35 U.S.C. 154(b) by 585 days.

(21) Appl. No.: 15/990,503

(22) Filed: May 25, 2018

(65) Prior Publication Data

US 2019/0358360 A1 Nov. 28, 2019

(51) Int. Cl.
| | |
|---|---|
| *A61L 15/28* | (2006.01) |
| *A61F 13/53* | (2006.01) |
| *A61L 15/20* | (2006.01) |
| *A61F 13/84* | (2006.01) |
| *A61L 15/46* | (2006.01) |
| *A61L 15/60* | (2006.01) |
| *B01D 15/00* | (2006.01) |
| *B01J 20/24* | (2006.01) |
| *B01J 20/28* | (2006.01) |
| *G01N 1/22* | (2006.01) |
| *G01N 33/00* | (2006.01) |

(52) U.S. Cl.
CPC .............. *A61L 15/28* (2013.01); *A61F 13/53* (2013.01); *A61F 13/8405* (2013.01); *A61L 15/20* (2013.01); *A61L 15/46* (2013.01); *A61L 15/60* (2013.01); *B01D 15/00* (2013.01); *B01J 20/24* (2013.01); *B01J 20/28023* (2013.01); *B01J 20/28035* (2013.01); *G01N 1/2226* (2013.01); *G01N 33/0047* (2013.01); *A61F 2013/530343* (2013.01); *A61F 2013/530481* (2013.01); *A61F 2013/8408* (2013.01); *G01N 2001/2229* (2013.01)

(58) Field of Classification Search
CPC .......... A61L 15/28; A61L 15/20; A61L 15/46; A61L 15/60; A61F 13/53; A61F 13/8405; A61F 2013/530343; A61F 2013/8408; B01D 15/00; B01J 20/24; B01J 20/28023; B01J 20/28035; G01N 1/2226; G01N 33/0047; G01N 2001/2229
USPC ........................................................ 210/690
See application file for complete search history.

(56) References Cited

U.S. PATENT DOCUMENTS

| | | |
|---|---|---|
| 4,865,855 A | 9/1989 | Hansen et al. |
| 4,980,294 A | 12/1990 | Elias et al. |
| 5,137,537 A | 8/1992 | Herron et al. |
| 5,300,192 A | 4/1994 | Hansen et al. |
| 5,308,896 A | 5/1994 | Hansen et al. |
| 5,352,480 A | 10/1994 | Hansen et al. |
| 5,447,977 A | 9/1995 | Hansen et al. |
| 5,547,541 A | 8/1996 | Hansen et al. |
| 5,547,745 A | 8/1996 | Hansen et al. |
| 5,571,618 A | 11/1996 | Hansen et al. |
| 5,589,256 A | 12/1996 | Hansen et al. |
| 5,607,759 A | 3/1997 | Hansen et al. |
| 5,609,727 A | 3/1997 | Hansen et al. |
| 5,611,885 A | 3/1997 | Hansen et al. |
| 5,614,570 A | 3/1997 | Hansen et al. |
| 5,641,561 A | 6/1997 | Hansen et al. |
| 5,672,418 A | 9/1997 | Hansen et al. |
| 5,693,411 A | 12/1997 | Hansen et al. |
| 5,749,863 A | 5/1998 | Payne |
| 5,789,326 A | 8/1998 | Hansen et al. |
| 5,807,364 A | 9/1998 | Hansen |
| 5,998,032 A | 12/1999 | Hansen et al. |
| 6,071,549 A | 6/2000 | Hansen |
| 6,231,721 B1 | 5/2001 | Quick et al. |
| 6,340,411 B1 | 1/2002 | Hansen et al. |
| 6,395,395 B1 | 5/2002 | Hansen et al. |
| 6,425,979 B1 | 7/2002 | Hansen et al. |
| 6,461,553 B1 | 10/2002 | Hansen et al. |
| 6,509,284 B1 | 1/2003 | Quincy, III et al. |
| 6,521,087 B2 | 2/2003 | Hansen et al. |
| 6,521,339 B1 | 2/2003 | Hansen et al. |
| 6,596,103 B1 | 7/2003 | Hansen et al. |
| 6,627,249 B2 | 9/2003 | Hansen et al. |
| 6,638,884 B2 | 10/2003 | Quick et al. |
| 6,652,845 B2 | 11/2003 | Hu et al. |
| 6,719,862 B2 | 4/2004 | Quick et al. |
| 6,767,553 B2 | 7/2004 | Sun et al. |
| 6,852,904 B2 | 2/2005 | Sun et al. |
| 7,018,490 B2 | 3/2006 | Hansen |

(Continued)

FOREIGN PATENT DOCUMENTS

| | | |
|---|---|---|
| CN | 101868258 A | 10/2010 |
| CN | 101903048 A | 12/2010 |

(Continued)

OTHER PUBLICATIONS

Examination Report dated Jul. 26, 2019, in AU Application No. 2018204635, filed May 25, 2018, 11 pages.
Examination Report dated Oct. 9, 2019, in Australian Application No. 2019208150, filed May 25, 2018, 8 pages.
Examination Report dated Sep. 28, 2020, in Australian Application No. 2019208150, filed May 25, 2018, 5 pages.
A. Brzezinski et al, Efficacy of a Novel pH-Buffering Tampon in Preserving the Acidic Vaginal pH During Menstruation, International Journal of Gynecology and Obstetrics, Jun. 2004, pp. 298-300, vol. 85 issue 3.

(Continued)

*Primary Examiner* — Edward M Johnson
(74) *Attorney, Agent, or Firm* — Thomas W. Barnes, III; Clifford R. Lamar, II (57) ABSTRACT

Absorbent materials configured to sequester trimethylamine (TMA), absorbent articles made therefrom, related methods of use, methods of measuring a reduction of free TMA, and related methods of making absorbent articles are described.

34 Claims, 1 Drawing Sheet

(56) References Cited

U.S. PATENT DOCUMENTS

| | | | |
|---|---|---|---|
| 7,144,474 B1 | 12/2006 | Hansen et al. | |
| 7,175,741 B2 | 2/2007 | West et al. | |
| 8,753,484 B2 | 6/2014 | Tan et al. | |
| 9,717,817 B2 | 8/2017 | Petersen | |
| 2003/0124171 A1* | 7/2003 | Sun | A61L 15/46 424/443 |
| 2003/0144637 A1* | 7/2003 | Sun | A61L 15/28 604/359 |
| 2004/0120921 A1* | 6/2004 | Quincy, III | A61L 9/014 424/76.21 |
| 2004/0122386 A1 | 6/2004 | Mocadlo | |
| 2004/0172001 A1 | 9/2004 | Tengberg et al. | |
| 2006/0029567 A1 | 2/2006 | Dutkiewicz | |
| 2007/0077428 A1 | 4/2007 | Hamed | |
| 2007/0142799 A1 | 6/2007 | Ales et al. | |
| 2008/0058739 A1 | 3/2008 | Roberts et al. | |
| 2009/0105676 A1 | 4/2009 | Brusk | |
| 2012/0079989 A1 | 4/2012 | Adamy | |
| 2013/0269890 A1 | 10/2013 | Dougherty et al. | |
| 2015/0182655 A1 | 7/2015 | Petersen | |
| 2016/0151257 A1 | 6/2016 | Klingman | |
| 2017/0172152 A1 | 6/2017 | Tan et al. | |
| 2017/0296693 A1 | 10/2017 | Petersen | |

FOREIGN PATENT DOCUMENTS

| | | |
|---|---|---|
| EP | 1034803 A1 | 9/2000 |
| EP | 1470827 A2 | 10/2004 |
| EP | 2 491 910 A1 | 8/2012 |
| JP | 52-85600 A | 7/1977 |
| JP | 56-160974 A | 12/1981 |
| JP | 2016169446 A | 9/2016 |
| KR | 10-2009-0046623 A | 5/2009 |
| KR | 101857746 B1 | 5/2018 |
| WO | 03/051413 A1 | 6/2003 |
| WO | 03051410 A1 | 6/2003 |
| WO | 2004/110876 A2 | 12/2004 |
| WO | 2007/149590 A2 | 12/2007 |
| WO | 2008058563 A1 | 5/2008 |
| WO | 2008/138386 A1 | 11/2008 |
| WO | WO-2009066255 A2 | 5/2009 |
| WO | 2009111768 A1 | 9/2009 |
| WO | 2010/088064 A2 | 8/2010 |
| WO | 2011103183 A1 | 8/2011 |
| WO | 2014/052055 A1 | 4/2014 |
| WO | 2015/048427 A1 | 4/2015 |
| WO | WO-2015048427 A1 | 4/2015 |
| WO | 2016/143217 A1 | 9/2015 |
| WO | 2015133267 A1 | 9/2015 |

OTHER PUBLICATIONS

Y. Liu, et al, Heterogeneous Uptake of Amines by Citric Acid and Humic Acid, Environmental Science and Technology, American Chemical Society, 2012, pp. 11112-11118.

T. Yasuhiko, et al, A new Color Test for the Measurement of Freshness of Fish by Volatile Bases Estimation, Tohoku Journal of Agriculture Research, Sep. 20, 1954, pp. 37-46, 5(1), http://hdl.handle.net/10097/29122.

International Search Report and Written Opinion dated Feb. 20, 2019, issued in corresponding Application No. PCT/US2018/034759, filed May 25, 2018, 23 pages.

Examination Report dated Apr. 23, 2019, in AU Application No. 2018204635, filed May 25, 2018, 16 pages.

Communication (Extended Search Report) dated Oct. 23, 2019, issued in corresponding European Application No. 19185867.9, filed Oct. 30, 2014, 6 pages.

Japanese Office Action dated Jul. 2, 2018, issued in corresponding Japanese Application No. 2014-214751, filed Oct. 21, 2014, 18 pages.

Notification of First Office Action dated Jul. 3, 2020, issued in Chinese Application No. 201711164813.4, filed Dec. 9, 2014, 17 pages.

Tsuchiya et al, "A new color test for the measurement of freshness of fish by volatile bases estimation", Tohoku journal of agricultural research, 1954, vol. 5(1), pp. 37-46.

* cited by examiner

METHODS OF REDUCING TRIMETHYLAMINE

BACKGROUND

Trimethylamine (TMA) is a chemical that has a strong, fishy odor even at low concentrations and is responsible for the fishy odor symptomatic of bacterial vaginosis.

An increase in pH of the vaginal environment is common during and following menstruation. Vaginal pH is usually 4-4.5; however, during menstruation vaginal pH can increase to 6.6. This increase in pH can encourage an overgrowth of anaerobic bacteria, sometimes resulting in an increase in the amount of TMA released from the more alkaline environment of the vagina.

Feminine hygiene products, such as sanitary pads, are products commonly used to absorb menstrual fluids, spotting, and urinary incontinence leakage. Because these products absorb fluids that may be malodorous (such as those that include TMA), are held close to the body with minimal air flow and are worn for several hours, malodor can become concentrated in these products. Therefore, TMA is a chemical of high interest in odor control for feminine hygiene products.

Currently, absorbent hygiene products promoted for odor control do so using fragrance, anti-bacterial properties, activated charcoal, or "Odor Lock" technology. However, conventional absorbent hygiene products do not specifically address malodors associated with TMA, such as by sequestration of TMA.

TMA is also associated with meat products, particularly fish products. Bacteria and fish enzymes convert TMA oxide present in fish into TMA. Absorbent pads included in meat packaging absorb meat juices and other liquids associated with meat products. However, conventional absorbent pads for meat packaging do not specifically sequester TMA or otherwise reduce TMA malodors associated with meat products.

Accordingly, there is a long-felt need for absorbent products that both absorb liquid and sequester TMA, thereby reducing TMA malodors. The present disclosure seeks to fulfill these needs and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In an aspect, the present disclosure provides a method of reducing free trimethylamine ("TMA") comprising contacting a TMA molecule with an absorbent material comprising a cellulosic fiber matrix and a carboxylic acid coupled to the cellulosic fiber matrix, wherein the reduction in free TMA is relative to a control.

In another aspect the present disclosure provides a method of sequestering TMA molecules comprising contacting the TMA molecules with an absorbent material comprising a cellulosic fiber matrix and a carboxylic acid coupled to the cellulosic fiber matrix.

In yet another aspect, the present disclosure provides an absorbent article comprising an absorbent material, wherein the absorbent material comprises a fiber matrix and a carboxylic acid coupled to the fiber matrix, wherein the fiber matrix comprises fibers selected from the group consisting of cellulose fibers and cellulose-based fibers, and wherein the absorbent article is a feminine hygiene product or a meat packaging pad.

In another aspect, the present disclosure provides a method of measuring a reduction of free TMA sequestered by an absorbent material comprising: contacting the absorbent material disposed in a container with an amount of TMA; withdrawing a portion of a gas headspace of the container; measuring an amount of free TMA in the withdrawn portion of the gas headspace; and determining a reduction in free TMA in the gas headspace relative to a control.

In yet another aspect, the present disclosure provides method of making an absorbent article comprising: preparing an absorbent material including a fiber matrix and a carboxylic acid coupled to the fiber matrix; and coupling a fluid-permeable top sheet and a fluid-impermeable back sheet to the absorbent material.

DESCRIPTION OF THE DRAWING

The foregoing aspects and many of the attendant advantages of the claimed subject matter will become more readily appreciated as the same become better understood by reference to the following detailed description, when taken in conjunction with the accompanying drawing, wherein:

The FIGURE graphically illustrates trimethylamine (TMA) levels in gas headspaces of containers holding absorbent materials in accordance with embodiments of the present disclosure and controls, each insulted with TMA solutions of different concentrations.

DETAILED DESCRIPTION

Figure 1:
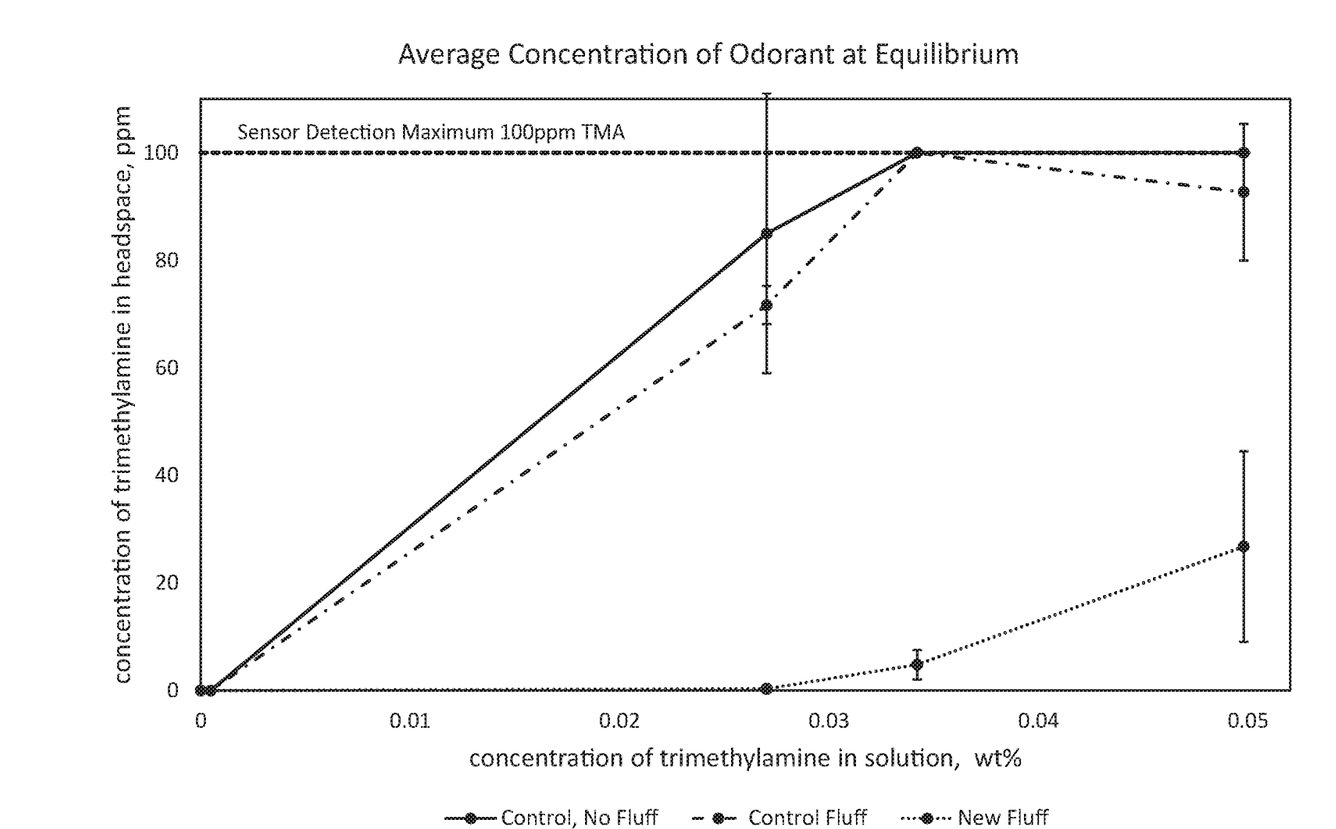

Described herein are absorbent materials configured to sequester trimethylamine (TMA), absorbent articles made therefrom, related methods of use, methods of measuring free TMA, methods of measuring a reduction of free TMA relative to a control, and related methods of making absorbent articles.

The detailed description set forth below, in connection with the appended drawing, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Absorbent Materials

In one aspect, the present disclosure provides an absorbent material configured to sequester TMA. As used herein "sequestration" refers to absorbing, adsorbing, reducing, binding, neutralizing, and/or eliminating TMA. In this regard, the absorbent materials described herein are configured to remove TMA from, for example, gas and liquid phases in contact with the absorbent materials by sequestration of the TMA. As discussed further herein, such sequestration reduces levels of free TMA in gas and liquid phases.

In an embodiment, the absorbent materials described herein comprise a fiber matrix and a carboxylic acid coupled to the fiber matrix. As described further herein, many carboxylic acids are water-soluble and, accordingly, may be amenable to aqueous or other solution-based processing to couple the carboxylic acid to the fiber matrix. Certain conventional absorbent materials use powders of non-carboxylic acid compositions, such as activated charcoal and activated carbon, for odor control. In practice, such powdered odor control components tend to clump, are often combustible, and may become airborne posing a contamination and inhalation risk.

Additionally, many carboxylic acids are readily available and inexpensive rendering them suitable for inclusion in products comprising absorbent materials. Furthermore, many carboxylic acids are also colorless, and thus may be included into absorbent materials without changing the color of, for example, fiber matrices of the absorbent materials. This is in contrast to certain conventional odor control components that have a dark color, such as activated charcoal and activated carbon, used in some conventional absorbent articles, which darken the color of the absorbent articles.

In an embodiment, the carboxylic acid is a polycarboxylic acid. In an embodiment, the polycarboxylic acid is a partially or fully neutralized salt. Without being bound by theory and as discussed further herein with respect to the figure and EXAMPLE 1, it is believed that the carboxylic acid groups of carboxylic acids aid in sequestration of TMA. Accordingly, because polycarboxylic acids have two or more carboxylic acids groups per carboxylic acid molecule, it is believed that each polycarboxylic acid molecule is configured to aid in sequestration of more TMA molecules than, for example, a monocarboxylic acid.

In an embodiment, the carboxylic acid is selected from the group consisting of malic acid, tartaric acid, salicylic acid, succinic acid, formic acid, pyruvic acid, proprionic acid, butyric acid, isobutyric acid, glycolic acid, salts thereof, and combinations thereof. In yet another an embodiment, the carboxylic acid is selected from the group consisting of citric acid, lactic acid, malic acid, tartaric acid, salicylic acid, succinic acid, formic acid, pyruvic acid, proprionic acid, butyric acid, isobutyric acid, glycolic acid, salts thereof, and combinations thereof. In another embodiment, the carboxylic acid is selected from the group consisting of citric acid, lactic acid, salts thereof, and combinations thereof. In an embodiment, the carboxylic acid is citric acid or a salt thereof.

In an embodiment, carboxylic acid salts include carboxylic acid salts selected from the group consisting of sodium salts, potassium salts, ammonium salts, other metal salts, and combinations thereof.

In an embodiment, the absorbent material comprises a carboxylic acid content of between about 0.01 wt % and about 10 wt % (also written herein as % by weight). In an embodiment, the absorbent material comprises a carboxylic acid content of between about 0.05% by weight and about 5% by weight. In an embodiment, the absorbent material comprises a carboxylic acid content of between about 0.1% by weight and about 1% by weight. In an embodiment, the absorbent material comprises a carboxylic acid content of about 0.01%, 0.02%, 0.03%, 0.04%, 0.05%, 0.06%, 0.07%, 0.08%, or 0.09% by weight. In an embodiment, the absorbent material comprises a carboxylic acid content of about 0.1%, 0.2%, 0.3%, 0.4%, 0.5%, 0.6%, 0.7%, 0.8%, or 0.9% by weight. In an embodiment, the absorbent material comprises a carboxylic acid content of about 1%, 2%, 3%, 4%, 5%, 6%, 7%, 8%, or 9% by weight.

Additionally, because the absorbent materials and absorbent articles described herein sequester TMA, components that mask TMA malodors (such as fragrances) are not necessary to reduce a TMA malodor. Accordingly, in an embodiment, the absorbent materials described herein do not comprise a fragrance. Such fragrance-free absorbent materials may be advantageous for users who, for example, have sensitivities or allergies to fragrances or prefer not to use products that include fragrances. It should also be noted that the absorbent materials and absorbent articles described herein can react with and sequester other basic molecules having a malodor.

In an embodiment, the fiber matrix comprises a cellulosic pulp structure. In an embodiment, the cellulosic pulp structure comprises a matrix of cellulose fibers, cellulose-based fibers, or combinations thereof and a carboxylic acid coupled to the fiber matrix. In an embodiment, the cellulose-based fibers are selected from the group consisting of viscose fibers, modal fibers, lyocell fibers, and combinations thereof. In an embodiment, the fiber matrix comprises a fluff pulp. In an embodiment, the fiber matrix comprises a Southern bleached softwood kraft pulp.

In an embodiment, the fiber matrix comprises synthetic fibers. In an embodiment, the fiber matrix comprises nonwoven synthetic fibers. In an embodiment, the fiber matrix comprises a mixture of synthetic fibers and natural fibers.

As discussed further herein, the absorbent materials described herein include a carboxylic acid coupled to a fiber matrix. In an embodiment, the carboxylic acid is directly coupled to the fiber matrix without, for example, a binder, a linker, or other intermediate composition or molecule between the carboxylic acid and the fiber matrix. In an embodiment, a carboxylic acid coupled to a fiber matrix includes a carboxylic acid covalently bound to the fiber matrix. In an embodiment, a carboxylic acid coupled to a fiber matrix includes a carboxylic acid non-covalently bound to the fiber matrix. Such non-covalent coupling can occur by, for example, hydrogen bonding, van der Waals forces, ionic bonds, and combinations thereof.

In an embodiment, the absorbent materials described herein do not comprise a binder, such as an organosilicone polymeric binder, coupled to the carboxylic acid and binding the carboxylic acid to the fiber matrix. Without being bound by theory, it is believed that the carboxylic acid is configured, in certain embodiments, to directly couple with the fiber matrix itself without the need for a binder. For example, in certain embodiments, the fiber matrix is a natural fiber comprising hydroxyl groups that couple with the carboxylic acid without a binder, such as an organosilicone polymeric binder.

In this regard, the absorbent materials and absorbent articles made therefrom that include a carboxylic acid directly coupled to the fiber matrix also do not require a pouch or other sealed container in order, for example, to contain a powder (such as activated charcoal or activated carbon) that might otherwise escape from the absorbent material or absorbent article.

In an embodiment, the carboxylic acid is applied to the fiber matrix in solid form, such as in powdered or granular forms. In an embodiment, the solid carboxylic acid is coupled to the fiber matrix with an adhesive. In an embodiment, the adhesive is a physical adhesive. In an embodiment, adhesive is a chemical adhesive.

In an embodiment, the solid carboxylic acid is applied to a fiber matrix that has a water content at or greater than the fiber saturation point ("FSP"), which is typically about 20% to about 25% water by weight. Without being bound by theory, it is believed that, in certain embodiments, the solid carboxylic acid at least partially dissolves when contacted with the wet fiber matrix and couples to the wet fiber matrix. Thus, water content from about 20% to about 99.9% water by weight for the fiber matrix in this embodiment is sufficient for at least partially dissolving the solid carboxylic acid.

In an embodiment, the absorbent materials described herein are free of or substantially free of an inorganic peroxide (in this case, it will be understood that "substantially free of an inorganic peroxide" refers to an amount of inorganic peroxide between 0 wt % and 1 wt % as limited by known detection methods).

TMA sequestration effects can also be observed by utilizing oxidized cellulosic fibers, which may be manufactured by a known method (see, e.g., U.S. Pat. No. 8,007,635, incorporated herein by reference in its entirety).

As above, the absorbent materials of the present disclosure are configured to sequester TMA. In an embodiment, the absorbent materials of the present disclosure are configured to sequester greater than or equal to about $6.15409 \times 10^{-5}$ g of TMA per about 1 g of absorbent material at a state of equilibrium (in this case, "equilibrium" should be understood to mean a time point at which TMA entering the gaseous headspace of the test apparatus reaches a steady state) at 25° C., wherein the absorbent material is treated with 0.01% by weight with a carboxylic acid selected from one of the groups provided herein. In an embodiment, the absorbent material is configured to sequester greater than or equal to about $6.15409 \times 10^{-5}$ g of TMA per about 1 g of absorbent material at a state of equilibrium at 25° C., wherein the absorbent material is treated with 0.01% by weight with citric acid.

As discussed further herein with respect to the methods of the present disclosure, in an embodiment, an amount of TMA sequestered by the absorbent materials described herein is determined by measuring an amount of TMA in a gas headspace of a closed container holding the absorbent material and an initial amount of TMA. In an embodiment, determining an amount of free TMA upon sequestration of TMA by the absorbent material includes contacting a known quantity of the absorbent material disposed in the closed container with an initial, known amount of TMA; withdrawing a portion of the gas headspace from the closed container after the absorbent material has been exposed to the initial amount of TMA and allowed to reach equilibrium within the gas headspace; and measuring the gaseous concentration of TMA in the withdrawn portion of the gas headspace (e.g., in ppm).

In an embodiment, the gas headspace has a volume of less than 1 L. In an embodiment, the gas headspace has a volume of about 0.5 L. In an embodiment, the container is a flexible container.

As discussed further herein, in an embodiment, the amount of TMA sequestered by the absorbent material is measured relative to a control absorbent material, such as a control absorbent material that does not comprise a carboxylic acid coupled to a fiber matrix, as discussed further herein with respect to EXAMPLE 1, or, alternatively, a control sample may be performed with a container that does not include any absorbent material (i.e., a null control).

In an embodiment, the absorbent materials described herein are configured to sequester TMA from a solution in contact with the absorbent material and sequester TMA from a gas phase in contact with the absorbent material. In this regard, the absorbent materials are configured to eliminate or reduce TMA malodors by sequestering both gaseous and dissolved or liquid TMA.

As discussed further herein, the absorbent materials of the present disclosure are configured to sequester TMA. In an embodiment, by way of quantifying the capability of TMA sequestration, the absorbent material is configured to reduce the gaseous concentration of free TMA within a gas headspace of a test apparatus (described in detail below) by 50% relative to a control (see above for discussion of appropriate controls). In an embodiment, the absorbent material is configured to reduce the amount of free TMA that enters (or otherwise would enter) the gas headspace by 75% relative to a control. In an embodiment, the absorbent material is configured to reduce the amount of free TMA that enters (or otherwise would enter) the gas headspace by 85% relative to a control. In an embodiment, the absorbent material is configured to reduce the amount of free TMA that enters (or otherwise would enter) the gas headspace by 90% relative to a control. In an embodiment, the absorbent material is configured to reduce the amount of free TMA that enters (or otherwise would enter) the gas headspace by 95% relative to a control. In an embodiment, the absorbent material is configured to reduce the amount of free TMA that enters (or otherwise would enter) the gas headspace by 99% relative to a control. In an embodiment, the absorbent material is configured to reduce the amount of TMA that enters (or otherwise would enter) the gas headspace by substantially 100% relative to a control (in this case, "substantially 100%" should be understood to mean an amount between 99% and 100% as limited by the detection method described herein).

As discussed further herein, in an embodiment, the cellulosic fiber matrix of the absorbent material is capable of reducing free TMA from a gas headspace by sequestration of the TMA. In an embodiment, the cellulosic fiber matrix of the absorbent material is capable of reducing free TMA by at least about 95 ppm in a gas headspace of about 0.5 L when the absorbent material comprises 0.45% by weight citric acid, the TMA is introduced in a liquid solution of about 0.034% by weight, and the control is an absorbent material consisting of a southern bleached softwood kraft fluff pulp of equal amount substantially free of any added carboxylic acids. In this case, "an equal amount" should be understood that to mean an amount of control fluff pulp having a mass of between 95% and 105% of the mass of the absorbent material as limited by known methods of detection.

In an embodiment, the cellulosic fiber matrix is capable of reducing free TMA by at least about 99% in a gas headspace of about 0.5 L when the absorbent material comprises 0.45%% by weight citric acid, the TMA is introduced in a liquid solution of about 0.027% by weight, and the control is an absorbent material consisting of a southern bleached softwood kraft fluff pulp of equal amount substantially free of any added carboxylic acids. In an embodiment, the cellulosic fiber matrix is capable of reducing free TMA by at least about 50% in a gas headspace of about 0.5 L when the absorbent material comprises 0.45%% by weight citric acid, the TMA is introduced in a liquid solution of about 0.05% by weight, and the control is an absorbent material consisting of a southern bleached softwood kraft fluff pulp of equal amount substantially free of any added carboxylic acids.

As discussed further herein with respect to the methods of reducing an amount of free TMA, in an embodiment, measuring a reduction of free TMA sequestered by an absorbent material of the present disclosure comprises contacting the absorbent material disposed in a container with an amount of TMA; withdrawing a portion of a gas headspace of the container; measuring an amount of free TMA in the withdrawn portion of the gas headspace; and determining a reduction in free TMA in the gas headspace relative to a control.

In an embodiment, the absorbent materials described herein may optionally further comprise an additive selected from the group consisting of activated charcoal, activated carbon, a fragrance, zeolites, and combinations thereof. While the absorbent materials of the present disclosure are configured to sequester TMA without such additives, in certain embodiments, the absorbent materials further comprise materials, including, but not limited to, activated charcoal, activated carbon, zeolites, or fragrances, configured, for example, to non-selectively absorb or mask certain other malodors or to supplement other TMA malodor control components of the absorbent materials.

In an embodiment, the absorbent material further comprises a superabsorbent polymer to aid in absorption of fluids.

Absorbent Articles

In another aspect, the present disclosure provides an absorbent article comprising an absorbent material of the present disclosure. As discussed further herein, odor control and prevention, particularly associated with TMA malodors, in feminine hygiene products and meat packaging products is of interest. Because the absorbent materials of the present disclosure are configured to sequester TMA they are particularly suitable for application in feminine hygiene products and meat packaging products.

Accordingly, in an embodiment, the absorbent article comprises a fiber matrix and a carboxylic acid coupled to the fiber matrix. In an embodiment, the fiber matrix comprises fibers selected from the group consisting of cellulose fibers, cellulose-based fibers, and combinations thereof.

In an embodiment, the absorbent article comprises a fluid-permeable top sheet. The fluid-permeable top sheet comprises a highly fluid-permeable material configured to move liquid, such as from a wearer, to the absorbent material. In an embodiment, the fluid-permeable top sheet comprises a material selected from the group consisting of hydrophilic woven materials, hydrophilic non-woven materials, airlaid sheets, wetlaid sheets, films comprising apertures, open cell foams, and batting.

In an embodiment, the absorbent article comprises a fluid-impermeable back sheet. The fluid-impermeable back sheet is configured to prevent liquid movement from the absorbent material through the fluid-impermeable sheet to, for example, clothing of a wearer.

In an embodiment, the absorbent material forms at least a portion of an absorbent core of the absorbent article. In an embodiment, the absorbent material is disposed between the fluid-permeable top sheet and the fluid-impermeable back sheet. In an embodiment, the fluid-permeable top sheet and fluid impermeable back sheet are suitably sealed enclosing the absorbent material. In an embodiment, the absorbent material is disposed within the fluid-permeable top sheet.

In an embodiment, the absorbent article is a feminine hygiene product. As described further herein, in an embodiment, the absorbent materials described herein comprise a fiber matrix and a carboxylic acid coupled to the fiber matrix. In this regard, without being bound by theory, it is believed that the absorbent articles comprising absorbent materials of the present disclosure reduce TMA malodors associated with vaginal fluids in at least two ways: (1) the carboxylic acid reduces vaginal pH, thereby inhibiting the growth of anaerobic bacteria, and (2) the carboxylic acid sequesters TMA molecules thereby reducing free TMA, as discussed further herein.

In an embodiment, the feminine hygiene product is selected from the group consisting of a panty liner, a sanitary napkin, a post-partum absorbent pad, a light incontinence pad, an interlabial pad, disposable menstrual protection underwear, and a tampon. In an embodiment, the feminine hygiene product is selected from the group consisting of a panty liner, a sanitary napkin, a post-partum absorbent pad, a light incontinence pad, an interlabial pad, and disposable menstrual protection underwear. In some embodiments, the absorbent articles of the present disclosure are not in the form of a tampon. Feminine hygiene products may be manufactured according to known methods (see for example U.S. Pat. No. 9,717,817, which is incorporated herein by reference in its entirety, and patents referenced therein).

In an embodiment, the feminine hygiene product is configured to be worn externally. As used herein, a feminine hygiene product configured to be worn externally is configured to be worn outside of a vagina. In an embodiment, the feminine hygiene product is not configured to be worn internally. As used herein, a feminine hygiene product configured to be worn internally is a feminine hygiene product configured to be worn at least partially within the vagina.

In an embodiment, the absorbent material in the feminine hygiene product comprises an absorbent material comprising a fiber matrix and a carboxylic acid coupled to the fiber matrix, wherein the absorbent material comprises a carboxylic acid content of between about 0.01 wt % and about 10 wt %.

In an embodiment, the absorbent article is a meat packaging pad. Meat packaging pads may include those known in the art and be manufactured according to known methods (see for example U.S. Pat. Nos. 5,908,649 and 7,655,829, which are incorporated herein by reference in their entirety). As described further herein, TMA malodors emanate from meat products, such as fish products, and there is a need to sequester TMA in meat packaging products. Because the absorbent materials described herein are configured to sequester TMA, they are particularly suitable for use in meat packaging products. In an embodiment, the meat packaging product is a meat packaging pad. In an embodiment, the meat packaging pad is a fish packaging pad. In an embodiment, the meat packaging pad including the absorbent material of the present disclosure is configured to absorb meat juices, such as fish juices, and other liquids, as well as sequester TMA.

In an embodiment, the absorbent material in the meat packaging pad comprises a fiber matrix and a carboxylic acid coupled to the fiber matrix, and wherein the absorbent material comprises a carboxylic acid content of between about 0.01 wt % and about 10 wt %. In an embodiment, the meat packaging pad comprises a superabsorbent polymer to aid in absorption of fluids. In an embodiment, the superabsorbent polymer is disposed within the absorbent material.

Method of Reducing Free TMA

As described further herein, TMA molecules, and TMA malodors arising therefrom, from, for example, vaginal fluids or meat juices, may be reduced through the sequestration of TMA by the absorbent materials or absorbent articles of the present disclosure. By sequestering TMA into the absorbent material or absorbent articles made therefrom, TMA malodor is reduced relative to an analogous scenario in which the TMA is not sequestered such that, for example, free TMA is present at a level that it cannot be smelled by a human nose or it can be smelled by a human nose at a greatly reduced level.

Accordingly, in another aspect, the present disclosure provides a method of reducing free TMA. As used herein, "free TMA" refers to an amount of TMA that is in a gas headspace or would equilibrate into a gas headspace and is capable of being measured and/or capable of being smelled by a human nose. Free TMA is in contrast to TMA molecules that are sequestered by, for example, an absorbent material or absorbent article, and, therefore, not available for measuring or detection by a human nose.

In an embodiment, the method of reducing levels of free TMA comprises contacting a TMA molecule with an absorbent material comprising a cellulosic fiber matrix and a carboxylic acid coupled to the cellulosic fiber matrix. In an embodiment, the method further comprises sequestering the TMA molecule.

As described further herein, the absorbent materials of the present disclosure and absorbent articles made therefrom are configured to sequester TMA from either or both a liquid phase and/or a gas phase. Accordingly, in an embodiment, contacting TMA with the absorbent material or the absorbent article comprises contacting TMA in a solution phase, such as TMA dissolved in vaginal fluids, menses, or meat juices. In an embodiment, the TMA molecule is in a liquid. In an embodiment, the liquid TMA is a TMA molecule dissolved in a solution or in a suspension. In an embodiment, the liquid TMA is a neat TMA liquid. In an embodiment, contacting TMA with the absorbent material or the absorbent article comprises contacting a menstrual fluid containing TMA with the absorbent material or the absorbent article. In an embodiment, contacting TMA with the absorbent material or the absorbent article comprises contacting a meat fluid, such as a fish fluid, containing TMA with the absorbent material or the absorbent article.

Correspondingly, in an embodiment, contacting TMA with the absorbent material or the absorbent article comprises contacting TMA in a gas phase, such as TMA volatilization from vaginal fluids, menses, or meat juices.

In an embodiment, the absorbent material is any absorbent material described herein. In an embodiment, the absorbent article is any absorbent article described herein. In an embodiment, the fiber matrix is a cellulosic fiber matrix (see below).

In an embodiment, the carboxylic acid is selected from the group consisting of malic acid, tartaric acid, salicylic acid, succinic acid, formic acid, pyruvic acid, proprionic acid, butyric acid, isobutyric acid, glycolic acid, salts thereof, and combinations thereof. In an embodiment, the carboxylic acid is selected from the group consisting of citric acid, lactic acid, malic acid, tartaric acid, salicylic acid, succinic acid, formic acid, pyruvic acid, proprionic acid, butyric acid, isobutyric acid, glycolic acid, salts thereof, and combinations thereof. In an embodiment, the carboxylic acid is citric acid or a salt thereof.

In an embodiment, the absorbent material comprises a carboxylic acid content of between about 0.01% by weight and about 10% by weight. In an embodiment, the absorbent material comprises a carboxylic acid content of between about 0.05% by weight and about 5% by weight. In an embodiment, the absorbent material comprises a carboxylic acid content of between about 0.1% by weight and about 1% by weight. In an embodiment, the absorbent material comprises a carboxylic acid content of about 0.01%, 0.02%, 0.03%, 0.04%, 0.05%, 0.06%, 0.07%, 0.08%, or 0.09% by weight. In an embodiment, the absorbent material comprises a carboxylic acid content of about 0.1%, 0.2%, 0.3%, 0.4%, 0.5%, 0.6%, 0.7%, 0.8%, or 0.9% by weight. In an embodiment, the absorbent material comprises a carboxylic acid content of about 1%, 2%, 3%, 4%, 5%, 6%, 7%, 8%, or 9% by weight.

In an embodiment, the fiber matrix comprises a cellulosic pulp structure. In an embodiment, the cellulosic pulp structure comprises a matrix of cellulose fibers, cellulose-based fibers, or combinations thereof and a carboxylic acid coupled to the fiber matrix. In an embodiment, the cellulose-based fibers are selected from the group consisting of viscose fibers, modal fibers, lyocell fibers, and combinations thereof. In an embodiment, the fiber matrix comprises a fluff pulp. In an embodiment, the fiber matrix comprises a Southern bleached softwood kraft pulp.

In an embodiment, the fiber matrix comprises synthetic fibers. In an embodiment, the fiber matrix comprises nonwoven synthetic fibers. In an embodiment, the fiber matrix comprises a mixture of synthetic fibers and natural fibers.

In an embodiment, contacting TMA with an absorbent material or an absorbent article made therefrom reduces at least 50% of the free TMA available to leave or re-enter into the absorbent material or absorbent article as a gaseous compound. In an embodiment, contacting TMA with an absorbent material or an absorbent article made therefrom reduces at least 75% of the free TMA available to leave or re-enter into the absorbent material or absorbent article as a gaseous compound. In an embodiment, contacting TMA with an absorbent material or an absorbent article made therefrom reduces at least 85% of the free TMA available to leave or re-enter into the absorbent material or absorbent article. In an embodiment, contacting TMA with an absorbent material or an absorbent article made therefrom reduces at least 95% of the free TMA available to leave or re-enter into the absorbent material or absorbent article. In an embodiment, contacting TMA with an absorbent material or an absorbent article made therefrom reduces at least 99% of the free TMA available to leave or re-enter into the absorbent material or absorbent article.

Method of Measuring a Reduction in Free TMA

In another aspect, the present disclosure provides a method of measuring a reduction of free TMA sequestered by an absorbent material, such as an absorbent material of the present disclosure or an absorbent article made therefrom. In an embodiment, the absorbent material is disposed in a closed container and is contacted with an amount of TMA. After the absorbent material has had an opportunity to sequester at least a portion of the amount TMA and, for example, the amount of TMA has reached an equilibrium between a gas headspace of the closed container and the absorbent material, a portion of the gas headspace is withdrawn from the closed container. In an embodiment, the amount of TMA is allowed to contact the absorbent material for sufficient time to reach equilibrium before a portion of the gas headspace is withdrawn from the closed container, thereby also providing sufficient time for at least a portion of the initial amount of TMA to be sequestered within the absorbent material. A person of ordinary skill in the art would readily know how to generate an equilibrium curve or other appropriate tool to monitor for and identify equilibrium.

In an embodiment, the closed container is a flexible container configured to at least partially collapse in response to the portion of the gas headspace being withdrawn. In this regard, it is easier for a user to withdraw the portion of the gas headspace from the closed container.

The withdrawn portion of the gas headspace is assayed to determine a gaseous concentration of free TMA present in the headspace. In an embodiment, measuring the amount of free TMA in the withdrawn portion comprises passing the withdrawn portion of the gas headspace over a stationary phase loaded with a colorimetric marker that changes color when contacted with TMA; and measuring an amount of color change in the stationary phase in response to passing the withdrawn portion of the gas headspace over the stationary phase. In an embodiment, assaying the withdrawn portion of the gas headspace to measure the gaseous concentration of free TMA comprises using a colorimetric gas detector tube, such as a Sensidyne® gas detector tube system. While colorimetric detection methods are described, it will be understood that other methods of TMA detection, for example, and not limited to, gas chromatography, can be used consistent with the methods of the present disclosure.

Reduction of free TMA is measured relative to a control. In an embodiment, the control is a null control, where a null control includes a control that does not include contacting a TMA molecule with an absorbent material. In an embodiment, the control is an absorbent material control, where an absorbent material control is an absorbent material having substantially no or no added carboxylic acid coupled to a fiber matrix (in this case, "substantially no added carboxylic acid" or "substantially free of added carboxylic acid" should be understood to mean no added carboxylic acid or an amount of added carboxylic acid between 0 wt % and 1 wt % as limited by known detection methods). As used herein, "added carboxylic acid" should be understood to mean an amount of carboxylic acid added or otherwise coupled to an absorbent material during processing or manufacturing over and above any carboxylic present in an untreated absorbent material. In an embodiment, the control absorbent material comprises a fluff pulp, such as a Southern bleached softwood kraft pulp, that has not been treated with or otherwise coupled to a carboxylic acid. In this regard, a user can determine an amount of TMA reduction by the carboxylic acid coupled to the fiber matrix of the absorbent materials described herein relative to the chosen control.

In an embodiment, an amount of TMA not sequestered by the absorbent material and allowed to equilibrate within the gaseous headspace ($TMA_g$) is compared to an amount of TMA not sequestered in a control experiment that is allowed to equilibrate within the control gaseous headspace ($TMA_c$). The reduction in gaseous concentration of free TMA measured in the headspace above the absorbent material relative to that of a control may be expressed as percent reduction of free TMA (% $TMA_{red}$). This percent reduction can be calculated with the following equation.

$$\% \ TMA_{red} = \frac{TMA_c - TMA_g}{TMA_c} \times 100\%$$

It should be noted that fluid containing TMA, such as a fluid used to insult an absorbent material or absorbent article, that resides on a side or other portion of the closed container may skew TMA reduction results. Such TMA-containing fluid that does not contact an absorbent material or absorbent article may result in increased volatilization of TMA from the TMA-containing solution into the gas headspace of the closed container. Such increased TMA volatilization may result in higher relative gaseous TMA concentrations than if the TMA-containing solution were insulted directly onto the absorbent material or absorbent article incorrectly indicating a capability (or lack thereof) of the absorbent material or absorbent article to sequester TMA.

Method of Sequestering TMA

As described further herein, the absorbent material and absorbent articles made therefrom are capable of sequestering TMA. Accordingly, in another aspect, the present disclosure provides a method of sequestering a TMA molecule. In an embodiment, the method of sequestering a TMA comprises contacting the TMA molecule with an absorbent material comprising a fiber matrix and a carboxylic acid coupled to the fiber matrix or an absorbent article made therefrom. In an embodiment, the method further comprises sequestering the TMA molecule in the absorbent material or absorbent article made therefrom.

In an embodiment, the absorbent material is any absorbent material described herein. In an embodiment, the absorbent article is any absorbent article described herein. In an embodiment, the fiber matrix is a cellulosic fiber matrix. In an embodiment, the cellulosic fiber matrix comprises a cellulosic pulp structure. In an embodiment, the cellulosic fiber matrix comprises fibers selected from the group consisting of cellulose fibers and cellulose-based fibers. In an embodiment, the cellulose-based fibers are selected from the group consisting of viscose fibers, modal fibers, lyocell fibers, and combinations thereof.

In an embodiment, the carboxylic acid is selected from the group consisting of malic acid, tartaric acid, salicylic acid, succinic acid, formic acid, pyruvic acid, proprionic acid, butyric acid, isobutyric acid, glycolic acid, salts thereof, and combinations thereof. In an embodiment, the carboxylic acid is selected from the group consisting of citric acid, lactic acid, malic acid, tartaric acid, salicylic acid, succinic acid, formic acid, pyruvic acid, proprionic acid, butyric acid, isobutyric acid, glycolic acid, salts thereof, and combinations thereof. In an embodiment, the carboxylic acid is citric acid or a salt thereof.

In an embodiment, the absorbent material comprises a carboxylic acid content of between about 0.01% by weight and about 10% by weight. In an embodiment, the absorbent material comprises a carboxylic acid content of between about 0.05% by weight and about 5% by weight. In an embodiment, the absorbent material comprises a carboxylic acid content of between about 0.1% by weight and about 1% by weight. In an embodiment, the absorbent material comprises a carboxylic acid content of about 0.01%, 0.02%, 0.03%, 0.04%, 0.05%, 0.06%, 0.07%, 0.08%, or 0.09% by weight. In an embodiment, the absorbent material comprises a carboxylic acid content of about 0.1%, 0.2%, 0.3%, 0.4%, 0.5%, 0.6%, 0.7%, 0.8%, or 0.9% by weight. In an embodiment, the absorbent material comprises a carboxylic acid content of about 1%, 2%, 3%, 4%, 5%, 6%, 7%, 8%, or 9% by weight.

In an embodiment, contacting the TMA molecule with the absorbent material or the absorbent article comprises contacting a liquid, such as a menstrual fluid, containing TMA with the absorbent material or the absorbent article made therefrom. In an embodiment, contacting the TMA molecule with the absorbent material comprises contacting a meat fluid containing the TMA molecule with the absorbent material or the absorbent article made therefrom. In an embodiment, the TMA molecule is in a gas phase, which contacts the absorbent material or absorbent article.

In an embodiment, the fiber matrices of the absorbent material of the present disclosure and absorbent articles made therefrom are capable of sequestering the TMA molecules such that a gas headspace of about 0.5 L at equilibrium contains less than about 1 ppm, 2 ppm, 3 ppm, 4 ppm, 5 ppm, 10 ppm, 20 ppm, 30 ppm, 40 ppm, or 50 ppm of free TMA when the absorbent material comprises 0.45% by weight citric acid. In an embodiment, the fiber matrices of the absorbent material of the present disclosure and absorbent articles made therefrom are capable of sequestering the TMA molecules such that a gas headspace of about 0.5 L at equilibrium contains less than about 50 ppm of free TMA at equilibrium when the absorbent material comprises 0.01% by weight citric acid and the TMA molecules are introduced in a liquid solution of between about 0.0005% by weight and about 0.034% by weight. In an embodiment, the fiber matrices of the absorbent material of the present disclosure and absorbent articles made therefrom are capable of sequestering the TMA molecules such that a gas headspace of about 0.5 L at equilibrium contains less than about 50 ppm of free TMA when the absorbent material comprises 0.01% by weight citric acid and the TMA molecules are introduced in a liquid solution of about 0.0005%, 0.001%, 0.005%, 0.01%, 0.015%, 0.02%, 0.025%, 0.027%, 0.03%, 0.034%, or 0.035% by weight. In an embodiment, the cellulosic fiber matrix is capable of sequestering the TMA molecules such that a gas headspace of about 0.5 L at equilibrium contains less than about 10 ppm of free TMA when the absorbent material comprises 0.01% by weight citric acid and the TMA molecules are introduced in a liquid solution of about 0.034% by weight. In an embodiment, the cellulosic fiber matrix is capable of sequestering the TMA molecules such that a gas headspace of about 0.5 L at equilibrium contains less than about 5 ppm of free TMA when the absorbent material comprises 0.01% by weight citric acid and the TMA molecules are introduced in a liquid solution of about 0.027% by weight.

In an embodiment, the cellulosic fiber matrix is capable of reducing free TMA by at least about 95 ppm in a gas headspace of about 0.5 L when the absorbent material comprises 0.01% by weight citric acid, the TMA is introduced in a liquid solution of about 0.034% by weight, and the control is an absorbent material consisting of a southern bleached softwood kraft fluff pulp of equal amount substantially free of any added carboxylic acids.

In an embodiment, wherein the cellulosic fiber matrix is capable of reducing free TMA by at least about 99% in a gas headspace of about 0.5 L when the absorbent material comprises 0.01% by weight citric acid, the TMA is introduced in a liquid solution of about 0.027% by weight, and the control is an absorbent material consisting of a southern bleached softwood kraft fluff pulp of equal amount substantially free of any added carboxylic acids. In an embodiment, the cellulosic fiber matrix is capable of reducing free TMA by at least about 50% in a gas headspace of about 0.5 L when the absorbent material comprises 0.01% by weight citric acid, the TMA is introduced in a liquid solution of about 0.05% by weight, and the control is an absorbent material consisting of a southern bleached softwood kraft fluff pulp of equal amount substantially free of any added carboxylic acids.

In an embodiment, determining an amount of free TMA after TMA has been sequestered by the absorbent materials described herein includes contacting the absorbent material disposed in a container with an initial amount of TMA in a liquid solution; withdrawing a portion of a gas headspace of the container; measuring an amount of free TMA in the withdrawn portion of the gas headspace, e.g., in ppm units. The measuring step can be performed in any suitable manner, including solid phase colorimetric gas detection tube described herein, gas chromatography, or others. Without being bound by theory, it is believed that TMA in a liquid solution in contact with the absorbent materials will react with the carboxylic acid and be reduced to a salt of a $RCOO^-N^+(Me)_3$, thus sequestering TMA by decreasing the available TMA for volatilization and equilibrating into the gas headspace of the experimental container apparatus, and thereby eliminating the TMA malodor.

Method of Making an Absorbent Article

As described further herein, the absorbent materials of the present disclosure and absorbent articles made therefrom are suitable as, for example, absorbent cores or other absorbent portions of absorbent articles, such as feminine hygiene products, because of their ability to sequester TMA. Accordingly, in another aspect, the present disclosure provides a method of making an absorbent article, such as a feminine hygiene product and a meat packaging pad, comprising an absorbent material of the present disclosure. In an embodiment, the method comprises preparing an absorbent material including a fiber matrix and a carboxylic acid coupled to the fiber matrix; and coupling a fluid-permeable top sheet and a fluid-impermeable back sheet to the absorbent material. In an embodiment, preparing an absorbent material comprises forming a cellulosic pulp structure by forming a cellulose pulp sheet from a cellulose pulp slurry, and forming a matrix of cellulose fibers from the cellulose pulp sheet. In an embodiment, a carboxylic acid is added by applying the acid in aqueous form to the pulp sheet. As also described further herein, in an embodiment, the carboxylic acid is added in a solid form, such as with a binder or adhesive.

In an embodiment, the absorbent material is any absorbent material described herein including a fiber matrix and a carboxylic acid coupled to the fiber matrix. In an embodiment, the fluid-permeable top sheet is any fluid-permeable top sheet described herein. In an embodiment, the fluid-impermeable back sheet is any fluid-impermeable back sheet described herein.

In an embodiment, the fluid-permeable top sheet and the fluid-impermeable back sheet are coupled to the absorbent material by a coupling method selected from the group consisting of stitching, coupling with an adhesive, heat sealing, ultrasonic welding, and combinations thereof.

In an embodiment, the fluid-permeable top sheet and the fluid-impermeable back sheet are coupled around the absorbent material and the absorbent material is disposed between the fluid-permeable top sheet and the fluid-impermeable back sheet. In this regard, the absorbent material forms at least a portion of an absorbent core of the absorbent article. In an embodiment, the absorbent material is disposed within the fluid-permeable top sheet.

In an embodiment, the feminine hygiene product is selected from the group consisting of a panty liner, a sanitary napkin, a post-partum absorbent pad, a light incontinence pad, an interlabial pad, disposable menstrual protection underwear, and a tampon. In an embodiment, the feminine hygiene product is selected from the group consisting of a panty liner, a sanitary napkin, a post-partum absorbent pad, a light incontinence pad, an interlabial pad, and disposable menstrual protection underwear. In some embodiments, the absorbent articles of the present disclosure are not in the form of a tampon. Feminine hygiene products may be manufactured according to known methods (see for example U.S. Pat. No. 9,717,817, which is incorporated herein by reference in its entirety).

In an embodiment, the feminine hygiene product is configured to be worn externally. In an embodiment, the feminine hygiene product is not configured to be worn internally.

In an embodiment, the absorbent article is a meat packaging pad. In an embodiment, the meat packaging pad is a fish packaging pad. Meat packaging pads may include those known in the art and be manufactured according to known methods (see for example U.S. Pat. Nos. 5,908,649 and 7,655,829, which are incorporated herein by reference in their entirety).

EXAMPLES

Example 1: Sequestration of TMA with a Fluff Pulp Treated with Citric Acid

Fluff pulp treated with citric acid (0.45 wt %) and untreated fluff pulp were fiberized, formed into pads, placed in sealed containers, and insulted with TMA solution. The untreated fluff pulp is from the same mill as the fluff pulp treated with citric, but does not contain the buffering treatment.

Fluff pulp sheets were fiberized and the fluff pulp was then formed into 2-inch diameter pads with an average weight of 0.94±0.02 g. These pads were compressed in a press to a pressure of 2000 psi.

Testing containers were constructed from 500 mL water bottles, which were selected due to their compressibility. 16 gauge needles were driven through plastic lids of the water bottles, glued in place, and sealed with silicone caulking. Rubber tubing was placed around the hilt of the needles to allow for an airtight seal between the hilt and measurement devices.

The compressed fluff rounds were introduced into the testing containers, insulted with 15 g of solution, sealed, and then the headspace above was tested for TMA after 2 hours. TMA solutions were tested at four concentrations: 0.0005%, 0.027%, 0.034%, and 0.05% by weight. Normal vaginal fluid not associated with bacterial vaginosis has TMA levels 0.0005% by weight according to literature values.

TABLE 1

TMA solutions

|  | g DI water | μL 25% solution | % by weight TMA solutions |
|---|---|---|---|
| literature value for healthy vaginal fluid | 1000 | 20 | 0.0005 |
| 58x literature | 300.2 | 347 | 0.027 |
| 73x literature | 300.02 | 439 | 0.034 |
| 106x literature | 300 | 639 | 0.05 |

The concentration of TMA in the headspace of the containers was tested above both control and test pulps two hours after insult. 105SE model Sensidyne® tubes were used. These tubes are labelled for use with ammonia, but are able to be used with TMA, as well. The actual TMA concentration is found by multiplying the Sensidyne® reading by a conversion factor of 0.5.

Twenty-five total samples were tested: eleven untreated control fluff pulp samples and fourteen test fluff pulp samples treated with citric acid. A minimum of two samples per concentration were averaged. Three or more samples per concentration were tested when the first two results varied. The twenty-five samples were allowed to interact with the TMA insult for approximately two hours at 25° C. to ensure equilibration before TMA in the container gas headspace was measured.

The TMA concentrations in headspaces above pads were compared for the test fluff pulp treated with citric acid and untreated control fluff pulp. It was found that the fluff pulp treated with citric acid decreased the headspace concentration of TMA in varying amounts, as summarized in TABLE 2 and the figure. As shown, the citric acid-treated fluff was found to eliminate TMA volatilization at literature concentrations in healthy vaginal fluid, at 0.0005% by weight, as well as at sixty times this concentration at 0.027% by weight. At 0.034% by weight, seventy times literature value, citric acid-treated fluff was found to reduce odorant volatilization into headspace 95% on average. The ability of citric acid-treated fluff to consistently inhibit TMA volatilization into headspace was not overwhelmed until a concentration of TMA 100 times that found in healthy vaginal fluid, at 0.05% by weight. Even at this concentration, the citric acid-treated fluff had a headspace odorant level on average 71.1% less than that of untreated fluff.

TABLE 2

Reduction of Free TMA in Headspace After Contact with Treated and Untreated Fluff Pulps.

| | Average Concentration of TMA in Headspace (# of samples) in ppm | | % Reduction = |
|---|---|---|---|
| % wt TMA Solution | Treated fluff | Untreated fluff | $\frac{\text{Untreated} - \text{treated fluff}}{\text{Untreated}} * 100\%$ |
| 0.0005 | 0 (2) | 0 (2) | N/A |
| 0.027 | 0.33 (3) | 71.7 (3) | 99.5% |
| 0.034 | 4.83 (3) | 100 (3) | 95.2% |
| 0.05 | 26.8 (5) | 92.7 (3) | 71.1% |

At 0.027% TMA solution, the average concentration of TMA in the headspace for the citric acid-treated fluff pads was 0.33 ppm. Untreated pulp had an average concentration of TMA in the headspace of 72 ppm TMA. The citric acid-treated fluff reduced the TMA in the headspace by 99.5%.

At 0.034% TMA solution, citric acid-treated fluff had an average concentration of TMA in the headspace reading of 5 ppm; untreated pulp had an average TMA level of 100 ppm in the gas headspace. It is noted that the detection limit of the Sensidyne® tubes is 100 ppm. Accordingly, the actual average TMA level in the gas headspace may have been higher than 100 ppm. The citric acid-treated fluff reduced TMA in headspace readings by at least 95%.

At 0.05% solution, citric acid-treated fluff had an average concentration of TMA in the headspace reading of 26.8 ppm. However, citric acid-treated fluff readings at this concentration ranged from 10 to 51 ppm. In contrast, the largest variation between any other two sample points at the other concentrations was 7 ppm (between 68 ppm and 75 ppm for untreated pulp at 0.03%).

The TMA concentrations in headspace above untreated fluff were above the maximum reading of the sensor for two of the three readings taken. As it is not possible to know the exact concentration, these data have been reported as a 100 ppm sensor reading. An estimation may be made for how much higher than the maximum reading the actual concentration is, based on how quickly the sensor reaches its maximum value, how far past the maximum the colorimetric reading has stopped, and on the malodor encountered by the tester (TMA has a fishy malodor at low concentrations, but an ammonia-like odor at high concentrations), but this is merely an estimation. These observations have been recorded in the test records.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A method of reducing free trimethylamine ("TMA") comprising contacting a TMA molecule with an absorbent material comprising a cellulosic fiber matrix and a carboxylic acid coupled to the cellulosic fiber matrix, wherein the reduction in free TMA is relative to a control.

2. The method of claim 1, wherein the TMA molecule is in a liquid.

3. The method of claim 2, wherein the TMA molecule is in a menstrual fluid.

4. The method of claim 2, wherein the TMA molecule is in a meat fluid.

5. The method of claim 1, wherein the TMA molecule is in a gas.

6. The method of claim 1, wherein the control is a null control.

7. The method of claim 1, wherein the control is an absorbent material control.

8. The method of claim 1, wherein the cellulosic fiber matrix comprises a cellulosic pulp structure.

9. The method of claim 1, wherein the cellulosic fiber matrix comprises fibers selected from the group consisting of cellulose fibers and cellulose-based fibers.

10. The method of claim 9, wherein the cellulose-based fibers are selected from the group consisting of viscose fibers, modal fibers, lyocell fibers, and combinations thereof.

11. The method of claim 1, wherein the carboxylic acid is selected from the group consisting of malic acid, tartaric acid, salicylic acid, succinic acid, formic acid, pyruvic acid, proprionic acid, butyric acid, isobutyric acid, glycolic acid, salts thereof, and combinations thereof.

12. The method of claim 1, wherein the carboxylic acid is selected from the group consisting of citric acid, lactic acid, malic acid, tartaric acid, salicylic acid, succinic acid, formic acid, pyruvic acid, proprionic acid, butyric acid, isobutyric acid, glycolic acid, salts thereof, and combinations thereof.

13. The method of claim 1, wherein the carboxylic acid is citric acid or a salt thereof.

14. The method of claim 1, wherein the absorbent material comprises a carboxylic acid content of between about 0.01% by weight and about 10% by weight.

15. The method of claim 1, wherein the cellulosic fiber matrix is capable of reducing free TMA by at least about 95 ppm in a headspace of about 0.5 L when the absorbent material comprises 0.01% by weight citric acid, the TMA is introduced in a liquid solution of about 0.034% by weight, and the control is an absorbent material consisting of a southern bleached softwood kraft fluff pulp of equal amount substantially free of any added carboxylic acids.

16. The method of claim 1, wherein the cellulosic fiber matrix is capable of reducing free TMA by at least about 99% in a headspace of about 0.5 L when the absorbent material comprises 0.01% by weight citric acid, the TMA is introduced in a liquid solution of about 0.027% by weight, and the control is an absorbent material consisting of a southern bleached softwood kraft fluff pulp of equal amount substantially free of any added carboxylic acids.

17. The method of claim 1, wherein the cellulosic fiber matrix is capable of reducing free TMA by at least about 50% in a headspace of about 0.5 L when the absorbent material comprises 0.01% by weight citric acid, the TMA is introduced in a liquid solution of about 0.05% by weight, and the control is an absorbent material consisting of a southern bleached softwood kraft fluff pulp of equal amount substantially free of any added carboxylic acids.

18. The method of claim 1, wherein the reduction in free TMA is measured by a process comprising:
   contacting the absorbent material disposed in a container with an amount of TMA;
   withdrawing a portion of a gas headspace of the container;
   measuring an amount of free TMA in the withdrawn portion of the gas headspace; and
   determining a reduction in free TMA in the gas headspace relative to a control.

19. A method of sequestering TMA molecules comprising contacting the TMA molecule with an absorbent material comprising a cellulosic fiber matrix and a carboxylic acid coupled to the cellulosic fiber matrix.

20. The method of claim 19, wherein the TMA molecules are in a liquid.

21. The method of claim 20, wherein the TMA molecules are in a menstrual fluid.

22. The method of claim 20, wherein the TMA molecules are in a meat fluid.

23. The method of claim 19, wherein the TMA molecules are in a gas.

24. The method of claim 19, wherein the cellulosic fiber matrix comprises a cellulosic pulp structure.

25. The method of claim 19, wherein the cellulosic fiber matrix comprises fibers selected from the group consisting of cellulose fibers and cellulose-based fibers.

26. The method of claim 25, wherein the cellulose-based fibers are selected from the group consisting of viscose fibers, modal fibers, lyocell fibers, and combinations thereof.

27. The method of claim 19, wherein the carboxylic acid is selected from the group consisting of malic acid, tartaric acid, salicylic acid, succinic acid, formic acid, pyruvic acid, proprionic acid, butyric acid, isobutyric acid, glycolic acid, salts thereof, and combinations thereof.

28. The method of claim 19, wherein the carboxylic acid is selected from the group consisting of citric acid, lactic acid, malic acid, tartaric acid, salicylic acid, succinic acid, formic acid, pyruvic acid, proprionic acid, butyric acid, isobutyric acid, glycolic acid, salts thereof, and combinations thereof.

29. The method of claim 19, wherein the carboxylic acid is citric acid or a salt thereof.

30. The method of claim 19, wherein the absorbent material comprises a carboxylic acid content of between about 0.01% by weight and about 10% by weight.

31. The method of claim 19, wherein the cellulosic fiber matrix is capable of sequestering the TMA molecules such that a headspace of about 0.5 L at equilibrium contains less than about 50 ppm of free TMA when the absorbent material comprises 0.45%% by weight citric acid and the TMA molecules are introduced in a liquid solution of about 0.05% by weight.

32. The method of claim 19, wherein the cellulosic fiber matrix is capable of sequestering the TMA molecules such that a headspace of about 0.5 L at equilibrium contains less than about 10 ppm of free TMA when the absorbent material comprises 0.45% by weight citric acid and the TMA molecules are introduced in a liquid solution of about 0.034% by weight.

33. The method of claim 19, wherein the cellulosic fiber matrix is capable of sequestering the TMA molecules such that a headspace of about 0.5 L at equilibrium contains less than about 5 ppm of free TMA when the absorbent material comprises 0.45% by weight citric acid and the TMA molecules are introduced in a liquid solution of about 0.027% by weight.

34. The method of claim 31, wherein the amount of free TMA is measured by a process comprising:
 contacting the absorbent material disposed in a container with an amount of TMA in a liquid solution;
 withdrawing a portion of a gas headspace of the container; and
 measuring an amount of free TMA in the withdrawn portion of the gas headspace.

* * * * *